US 6,716,585 B2
United States Patent
Al-Mahmood

(10) Patent No.: US 6,716,585 B2
(45) Date of Patent: Apr. 6, 2004

(54) METHOD FOR IDENTIFYING NOVEL GENES INVOLVED IN THE REGULATION OF ANGIOGENESIS, STUDY OF SAID GENES AND USE THEREOF FOR THERAPEUTIC PURPOSES

(75) Inventor: Salman Al-Mahmood, Paris (FR)

(73) Assignee: GeneSignal (FR)

( * ) Notice: Subject to any disclaimer, the term of this patent is extended or adjusted under 35 U.S.C. 154(b) by 0 days.

(21) Appl. No.: 10/103,614

(22) Filed: Mar. 21, 2002

(65) Prior Publication Data

US 2003/0059796 A1 Mar. 27, 2003

Related U.S. Application Data

(63) Continuation of application No. PCT/FR00/02607, filed on Sep. 20, 2000.

(30) Foreign Application Priority Data

Sep. 21, 1999  (FR) .............................................. 99 11790

(51) Int. Cl.$^7$ .............................. C12Q 1/68; C12P 19/34
(52) U.S. Cl. ........................ 435/6; 435/91.1; 435/91.2
(58) Field of Search ........................... 435/6, 91.1, 91.2

(56) References Cited

U.S. PATENT DOCUMENTS

| | | | | |
|---|---|---|---|---|
| 6,433,138 | B1 | * | 8/2002 | Zimrin et al. ................ 530/350 |
| 2002/0015970 | A1 | * | 2/2002 | Murray et al. ............... 435/7.23 |
| 2002/0055099 | A1 | * | 5/2002 | Fisher ............................ 435/6 |

FOREIGN PATENT DOCUMENTS

| | | | |
|---|---|---|---|
| WO | WO 95/23968 | 9/1995 | |
| WO | 01/32926 | * 5/2001 | ............ C12Q/1/68 |

OTHER PUBLICATIONS

Glienke et al., Eur. J. Biochem. 267, 2820–2830 (May 2000).*
Kahn et al., Am. J. Pathol. 156(6), 1887–1900 (Jun. 2000).*
Yong Song Gho et al., *Development of Antiangiogenin Peptide Using a Phage–Displayed Peptide Library*, Cancer Research, vol. 57, Sep. 1, 1997, pp. 3733–3740.
Felicitas Pröls et al., *Differential Expression of Osteopontin, PC4, and CEC5, a Novel mRNA Species, during in vitro Angiogenesis*, Experimental Cell Research, vol. 239, 1998, pp. 1–10.
Toshihide Tanaka et al., *Viral–Vector–targeted Antiangiogenic Gene Therapy Utilizing an Angiostatin Complementary DNA*, Cancer Research, vol. 58, No. 15, Aug. 1, 1998, pp. 3362–3369.
R. Montesano et al., *Basic fibroblast growth factor induces angiogenesis in vitro*, Proceedings of the National Academy of Sciences USA, vol. 83, Oct. 1986, pp. 7297–7301.
David T. Shima et al., *Alterations in gene expression associated with changes in the state of endothelial differentiation*, Differentiation, vol. 58, 1995, pp. 217–226.
Slawomir Majewski et al., *Interleukin–12 Inhibits Angiogenesis Induced by Human Tumor Cell Lines In Vivo*, Journal of Investigative Dermatology, vol. 106, 1996, pp. 1114–1118.
Ann B. Zimrin et al., *An Antisense Oligonucleotide to the Notch Ligand Jagged Enhances Fibroblast Growth Factor–induced Angiogenesis in Vitro*, The Journal of Biological Chemistry, vol. 271 No. 51, Dec. 20, 1996, pp. 32499–32502.
Rangana Choudhuri et al., *An Angiogenic Role for the Neurokines Midkine and Pleiotrophin in Tumorigenesis*, Cancer Research, vol. 57, May 1, 1997, pp. 1814–1819.

* cited by examiner

*Primary Examiner*—Kenneth R. Horlick
(74) *Attorney, Agent, or Firm*—Piper Rudnick LLP

(57) ABSTRACT

A process for identifying genes coding for cellular constituents involved in regulating angiogenesis including culturing endothelial cells on an extracellular matrix protein according to at least four different types of conditions: a reference condition, an angiogenesis promoting condition, an angiogenesis inhibiting condition, and a control condition; isolating messenger RNAs stemming from cells cultured according to the different conditions; and comparing at the qualitative and/or quantitative level, different messenger RNA populations to identify messenger RNAs stemming exclusively or in a particularly elevated quantity from cell cultures under conditions stimulating and/or inhibiting angiogenesis, the messenger RNAs corresponding to the genes coding for the cellular constituents involved in regulating angiogenesis.

8 Claims, 4 Drawing Sheets

Denaturing electrophoresis:

Extraction of the bands of interest
Reamplification, purification

Probe for
hybridization
by Northern Blot
method

Probe for
screening
cDNA libraries

Subcloning
and sequencing

SEQUENCE LISTING

```
<160> NUMBER OF SEQ ID NOS: 5

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 1 ttttttttttt ttgg                                                    14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 2
```

-continued

```
tttttttttt ttag                                                    14

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 3
tttttttttt ttcg                                                    14

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (1)
<223> OTHER INFORMATION: a, t, c or g
<220> FEATURE:
<221> NAME/KEY: modified_base
<222> LOCATION: (19)
<223> OTHER INFORMATION: a, t, c or g

<400> SEQUENCE: 4
nvaaaaaaaa aaaaaaaan                                               19

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (13)
<223> OTHER INFORMATION: a, t, c or g

<400> SEQUENCE: 5
tttttttttt tvn                                                     13
```

METHOD FOR IDENTIFYING NOVEL GENES INVOLVED IN THE REGULATION OF ANGIOGENESIS, STUDY OF SAID GENES AND USE THEREOF FOR THERAPEUTIC PURPOSES

RELATED APPLICATIONS

This is a continuation of International Application No. PCT/FR00/02607, with an international filing date of Sep. 20, 2000, which is based on French Patent Application No. FR 99/11790, filed Sep. 21, 1999.

FIELD OF THE INVENTION

This invention relates to the identification of new genes coding for cellular constituents involved in the regulation of angiogenesis. The invention relates more specifically to a process for the identification of these genes. The invention also relates to the use of the factors coded by the identified genes for the clinical study of the angiogenesis process, for the diagnosis and treatment of pathologies linked to this process as well as for pharmacological, pharmacogenomic or drug identification trials.

BACKGROUND

Angiogenesis is the fundamental process by which new blood vessels are formed. This process is essential in numerous normal physiological phenomena such as reproduction development and cicatrization. In these normal biological phenomena, angiogenesis is under strict control, i.e., it is triggered during a short period of time, several days, then completely inhibited. However, numerous pathologies are linked to invasive, uncontrolled angiogenesis. Arthritis, for example, is a pathology caused by damage to cartilage by invasive neovessels. In diabetic retinopathy, the invasion of the retina by neovessels leads to blindness in the patients. Neovascularization of the ocular apparatus is a major cause of blindness and such neovascularization is responsible for around twenty different diseases of the eye. Finally, the growth and metastasis of tumors is directly linked to neovascularization and is dependent on angiogenesis. The tumor stimulates the growth of the neovessels for its own growth. Moreover, these neovessels provide escape routes allowing the tumors to reach the blood circulation and cause metastases at remote sites such as the liver, lungs and bones.

In other pathologies such as the cardiovascular diseases, the diseases of the peripheral arteries as well as the vascular and cerebral lesions, angiogenesis can present an important therapeutic base. In fact, the promotion of angiogenesis in the damaged locations can lead to formation of sanguineous neovessels that are lateral and alternative to the damaged vessels, thereby providing blood and, thus, oxygen and other nutritive and biological factors necessary for the survival of the tissues involved.

Formation of neovessels by endothelial cells involves migration, growth and differentiation of endothelial cells. Regulation of these biological phenomena is directly linked to the genetic expression. With regard to angiogenesis, a constantly growing number of studies show that the regulation of angiogenesis is implemented via an equilibrium among the factors acting directly on the endothelial cell. These factors can be stimulating factors, on the one hand, such as VEGF, FGFs, IL-8, HGF/SF, PDGF, etc. They can also be inhibitory factors such as IL-10, IL-12, gro-α and β, platelet factor 4, angiostatin, human chondrocyte-derived inhibitor, thrombospondin, leukemia inhibitory factor, etc. (Jensen, Surg. Neural., 1998, 49, 189–195; Tamatani et al., Carcinogenesis, 1999, 20, 957–962; Tanaka et al., Cancer Res., 1998, 58, 3362–3369; Ghe et al., Cancer Res., 1997, 57, 3733–3740; Kawahara et al., Hepatology, 1998, 28, 1512–1517; Chandhuni et al., Cancer Res., 1997, 57, 1814–1819; Jendraschak and Sage, Semin. Cancer Biol., 1996, 7, 139–146; Majewski et al., J. Invest. Dermatol., 1996, 106, 1114–1119).

The control of angiogenesis, thus, represents a strategic axis both for fundamental research to improve comprehension of the numerous pathological phenomena linked to angiogenesis, as well as a foundation for the development of new therapies for treating pathologies linked to angiogenesis.

SUMMARY OF THE INVENTION

This invention relates to a process for identifying genes coding for cellular constituents involved in regulating angiogenesis including culturing endothelial cells on an extracellular matrix protein according to at least four different types of conditions: a reference condition, an angiogenesis promoting condition, an angiogenesis inhibiting condition, and a control condition; isolating messenger RNAs stemming from cells cultured according to the different conditions; and comparing at the qualitative and/or quantitative level, different messenger RNA populations to identify messenger RNAs stemming exclusively or in a particularly elevated quantity from cell cultures under conditions stimulating and/or inhibiting angiogenesis, the messenger RNAs corresponding to the genes coding for the cellular constituents involved in regulating angiogenesis.

This invention also relates to a pharmaceutical composition for diagnosing and/or treating pathologies linked to angiogenesis including a gene involved in regulating angiogenesis identified by the process for identifying genes coding for cellular constituents involved in regulating angiogenesis including culturing endothelial cells on an extracellular matrix protein according to at least four different types of conditions: a reference condition, an angiogenesis promoting condition, an angiogenesis inhibiting condition, and a control condition; isolating messenger RNAs stemming from cells cultured according to the different conditions; and comparing at the qualitative and/or quantitative level, different messenger RNA populations to identify messenger RNAs stemming exclusively or in a particularly elevated quantity from cell cultures under conditions stimulating and/or inhibiting angiogenesis, the messenger RNAs corresponding to the genes coding for the cellular constituents involved in regulating angiogenesis.

This invention further relates to a laboratory kit for diagnosing and/or treating pathologies linked to angiogenesis, including products and reagents for culturing endothelial cells on an extracellular matrix protein in combination with one or more angiogenic and anti-angiogenic factors.

DETAILED DESCRIPTION

Figure 1:
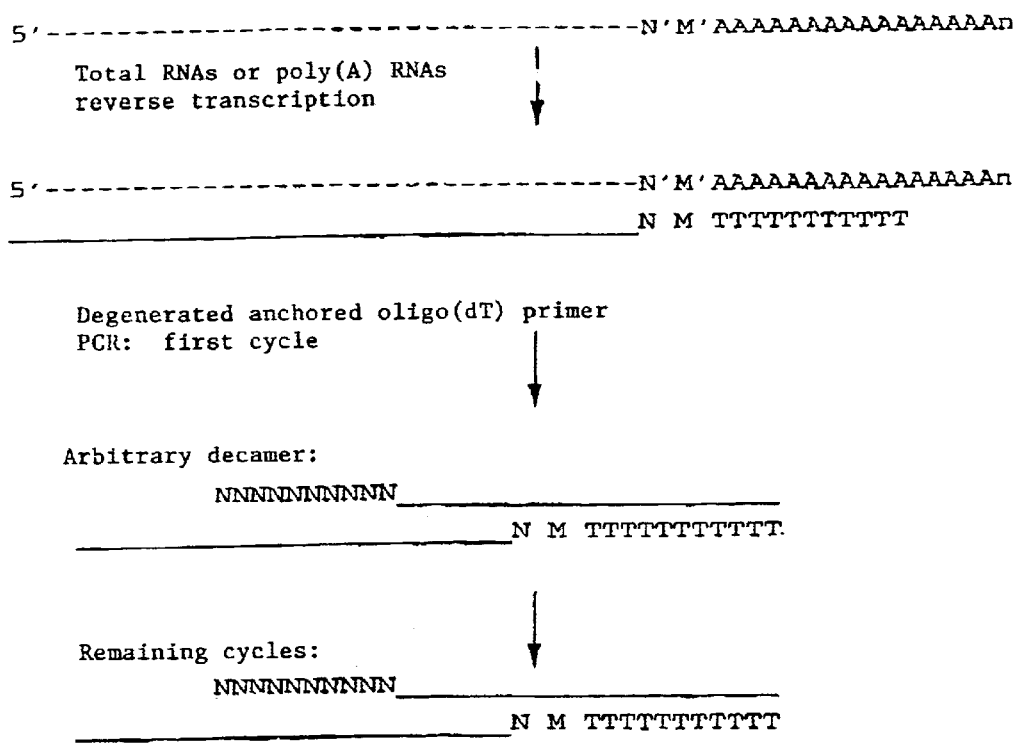
FIGS. 1A and 1B schematically show a differential display method in accordance with aspects of the invention.
Figure 1:
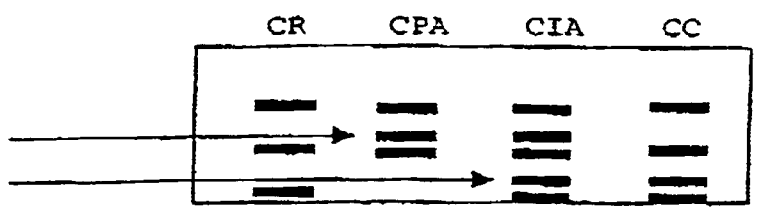

Numerous pharmaceutical groups have developed therapeutic strategies for controlling angiogenesis based directly on the use of paracrine signals, the stimulatory and inhibitory factors, as agents for promoting or inhibiting angiogenesis. These strategies are based essentially on the use of these factors in their protein form as agents stimulating or inhibiting angiogenesis or, more recently, in the form of expression vectors coding for the selected factors.

The discovery of new molecules that can serve as active principles useful in the treatment of pathologies linked to angiogenesis is facilitated if one has available models of studies that make it possible to perform in vitro experimentation.

It is possible to culture endothelial cells. A first culture method consists of causing the cells to adhere to the flat bottom of a culture flask, where cells are immersed in a culture medium, and then incubating them until obtaining a confluent carpet of cells. Other culture methods are characterized by causing the endothelial cells to adhere to the flat bottom of a culture flask previously covered by a layer of a protein belonging to the family of proteins called extracellular matrix proteins. Still other methods involve covering the endothelial cells with a lattice obtained by retracting a protein of this family such as collagen or fibrin, thereby forming a lattice of collagen or fibrin, respectively.

No matter which technique is employed in culturing endothelial cells, after a certain period of incubation one obtains a monolayer of a homogeneous cellular population. Nevertheless, each population obtained in this manner has an organization which is not related to that of the differentiated endothelial cells forming neovessels.

It has already been shown that it is possible when culturing endothelial cells under a collagen or fibrin lattice to obtain differentiated endothelial cells forming capillary tubes in vitro, following stimulation of the layer of endothelial cells by one of the angiogenesis-promoting paracrine signals (Montesano et al., Proc. Natl. Acad. Sci. USA, 1986, 83, 7297–7301). These capillary tubes formed in vitro by stimulated endothelial cells are similar to the neovessels formed by the same cell type in vivo during angiogenesis. They thus constitute a model that is suitable for investigating new factors involved in the regulation of angiogenesis.

Regulation of angiogenesis takes place via an equilibrium between the action of the stimulatory factors and the action of the inhibitory factors. These factors, which themselves are the products of genetic expression, are mitogenic: they control the expression of multiple genes involved in regulating angiogenesis and can also be involved in other physiological or pathological processes. Thus, two families of genes are involved in regulating angiogenesis. First, there is the family of the first generation of genes coding for the stimulatory or inhibitory factors. Then, secondly, there is the family of genes coding for the cellular constituents intimately involved in the regulation of angiogenesis such as the cellular receptors, the extracellular matrix proteins, the docking proteins, the adapter proteins, the kinases, the phosphatases, the proteases, the glycosyl-transferases, etc. This family of genes thus constitutes a "family of the second generation of angiogenesis genes".

This invention pertains to a process for the identification of the genes coding for the cellular constituents intimately involved in the regulation of angiogenesis and belonging to the family of the second generation of angiogenesis genes. The term "cellular constituents" is understood to mean proteins, groups of proteins or assemblies of proteins of the type defined below for products coded by the genes of the second-generation families. The factors stimulating or inhibiting the process control the expression of genes involved in the augmentation or inhibition of angiogenesis. It is, therefore, necessary to study two types of profiles of genetic expression: the first is that of cells placed under angiogenesis stimulating conditions and the second corresponds to that of cells placed under angiogenesis inhibiting conditions.

Although the physiological state of cells under angiogenesis inhibiting conditions and that of unstimulated endothelial cells are similar, it is important to distinguish the expression of genes in the two cases. In fact, endothelial cells stimulated with a factor promoting angiogenesis such as FGF1, for example, and incubated with an angiogenesis inhibiting factor are not capable of forming neovessels. Moreover, numerous factors inhibiting angiogenesis are mitogenic agents and affect genetic expression, such as IL-10, IL-12, gro-$\alpha$ and $\beta$, etc. Thus, endothelial cells can have a genetic expression in angiogenesis inhibitory conditions which is different from the genetic expression of an unstimulated endothelial cell. It is, therefore, important to compare the profiles of genetic expression of the cells when they are placed under different culture conditions, angiogenesis stimulating conditions and angiogenesis inhibiting conditions, in relation to precisely defined reference culture conditions.

Identification of genes coding for the cellular constituents involved in the regulation of angiogenesis is made possible by the process according to the invention. This process comprises the following steps:

a) culturing endothelial cells on an extracellular matrix protein according to four different types of conditions: a reference condition, an angiogenesis promoting condition, an angiogenesis inhibiting condition and a control condition;

b) isolating the messenger RNAs stemming from the cells cultured according to the different conditions;

c) comparing at the qualitative and/or quantitative level of the different messenger RNA populations to identify the messenger RNAs stemming exclusively or in a particularly elevated quantity from cell cultures under conditions stimulating and/or inhibiting angiogenesis, the messenger RNAs corresponding to the genes coding for the cellular constituents involved in the regulation of angiogenesis;

d) optionally, isolating the messenger RNAs identified in step c), their amplification and their purification;

e) optionally, cloning and sequencing the nucleic acid molecules obtained in the preceding step;

f) identifying the gene(s) corresponding to the isolated nucleic acid molecules, comprising optionally expressing the genes in suitable systems and testing theprotein thereby produced for its properties in the regulation of angiogenesis.

In order to identify the members of the family of the second generation of genes involved in the regulation of angiogenesis, the inventors, therefore, determined four types of experimental culture conditions for endothelial cells:

the cells cultured under reference conditions (CR) are not stimulated;

the cells cultured under angiogenesis promoting conditions (CPA) are stimulated by an angiogenic factor which can be, for example, FGF1, FGF2, HGF, PDGF, etc.;

the cells cultured under angiogenesis inhibiting conditions (CIA) are stimulated by an angiogenic factor and incubated with one or more anti-angiogenic factors. The stimulating factor can be FGF2; the inhibitory factor can be, for example, selected from among IL-10, IL-12, the chemokines gro-α or β, etc.;

the cells cultured under control conditions (CC) are incubated with an anti-angiogenic factor which can be, for example, IL-10, IL-12, the chemokines gro-α, β and the like.

These experimental culture conditions are applied to endothelial cells cultured according to one of the procedures known in the field. The extracellular protein can be constituted by, among others, fibrin, collagen, laminin, Matrigel, fibronectin or any other protein belonging to the family of extracellular matrix proteins.

The factors capable of stimulating or inhibiting angiogenesis are selected from among the factors whose action on the angiogenesis process has been demonstrated (Jensen, Surg. Neural., 1998, 49, 189–195; Tamatani et al., Carcinogenesis, 1999, 20, 957–962; Tanaka et al., Cancer Res., 1998, 58, 3363–3369; Ghe et al., Cancer Res., 1997, 57, 3733–3740; Kawahara et al., Hepatology, 1998, 28, 1512–1517; Chandhuni et al., Cancer Res., 1997, 57, 1814–1819; Jendraschak and Sage, Semin. Cancer Biol., 1996, 7, 139–146; Majewski et al., J. Invest. Dermatol., 1996, 106, 1114–1119).

The angiogenesis stimulating factors employed in step a) of the process according to the invention are selected from among:

fibroblast growth factors 1 to 15 (FGF 1 to FGF 15)

epidermis growth factor (EGF)

vascular endothelial growth factor (VEGF)

hepatocyte growth factor (HGF)

platelet derivative growth factor (PDGF)

interleukin 8 (IL-8)

angiogenin transformant growth factor (TGF)

the neurokine midkine pleiotropin or any other angiogenesis-inducing factor of a protein nature.

The angiogenesis inhibiting factors employed in step a) of the process according to the invention are selected from among:

thrombospondin angiostatin endostatin platelet factor 4 interleukin 10 (IL-10)

interleukin 12 (IL-12)

the chemokines gro-α and β the human chondrocyte-derived inhibitor leukemia inhibitory factor tumor necrosis factor (TNF)

or any other angiogenesis-inhibiting factor of a protein nature.

The various factors regulating angiogenesis are added to the cell cultures according to procedures well known in the field (Montesano et al., Proc. Natl. Acad. Sci. USA, 1986, 83, 7297–7301). The effective concentrations to employ for each of the various factors are advantageously the following: from 1 ng/ml to 200 ng/ml.

In the process according to the invention, it is possible that one of more of the factors capable of stimulating or inhibiting angiogenesis is (are) added to the cell culture in the form of an expression vector constructed in a manner to enable the synthesis of the factor(s) in the cell culture. An example of a vector of this type is cited in Tanaka et al. (Cancer Res., 1998, 58, 3362–3369).

The process according to the invention comprises in step c) analysis of the profile of expression of the genes of the cells under angiogenesis stimulation or inhibition conditions. This analysis is based on the study of messenger RNAs of endothelial cells under angiogenesis stimulation or inhibition conditions by comparison with messenger RNAs of the cells under reference and control conditions. These messenger RNAs are extracted from the cells by conventional techniques (Vancopoulos et al., 1990, in "Methods for Cloning and Analysis of Eukaryotic Genes", p. 8–23, Ed. Jones and Bartlett, Boston) for isolating the RNAs from other cellular constituents. Messenger RNAs are isolated from other RNAs, for example, by extraction based on the presence of the poly-A sequence present at their ends.

Analysis of different messenger RNA populations can be performed by a differential display method comprising the following steps:

messenger RNAs are reverse transcribed,

DNA molecules obtained by reverse transcription are separated by electrophoresis, DNA molecules of interest are detected and then extracted from the electrophoresis support, DNA of interest is purified, and purified DNA can be used as a probe for screening a cDNA library; it can also be directly subcloned and sequenced.

The purified DNA can, in particular, be used as a probe for screening a cDNA library or for detecting a complementary nucleic acid by the Northern blot technique.

Differential display enables simultaneous detection of two groups of genes expressed differentially, for example, certain genes linked to an angiogenic factor selected from among (a), and other genes linked to an anti-angiogenic factor selected from among (b). The differential display technique also enables detection of rare mRNAs and minimizes redundancy and false positive clones.

In the process according to the invention, analysis of different messenger RNA populations can also be performed by subtractive hybridization. Subtractive hybridization includes isolating mRNAs, reverse transcription of the mRNAs, construction of cDNA libraries, subtraction and screening by differential hybridization. The two techniques are complementary and will be used to identify mRNAs in relation to angiogenesis.

The process according to the invention is remarkable in that it enables qualitative and quantitative assessment of angiogenesis under the effect of two types of paracrine signals—angiogenic and anti-angiogenic.

Moreover, this process makes it possible to test the effect of different proteins as extracellular matrix (fibrin, collagen, laminin, Matrigel, fibronectin, etc.) in combination with the paracrine signals. Furthermore, the process can easily be modified to include another type of cell in addition to endothelial cells.

Another aspect of the invention consists of using a factor identified by means of the process in a pharmaceutical composition intended for diagnosis and/or treatment of pathologies linked to angiogenesis such as, for example, arthritis, diabetic retinopathy, cancer or cardiovascular diseases. A factor identified by means of the process according to the invention can also be used for the purpose of pharmacological, pharmacogenomic or drug identification trials.

A supplementary aspect of the invention consists of a laboratory kit for the implementation of the process. Such a kit comprises the products and reagents useful for culturing endothelial cells on an extracellular matrix protein in combination with one or more angiogenic and anti-angiogenic factors. In the case of a laboratory kit intended for diagnostic purposes, one or more factors among the angiogenic and anti-angiogenic factors can advantageously be replaced by the patient's serum.

Other advantages and characteristics of the invention will become manifest upon reading the examples below, presented on a nonlimitative basis and with reference to FIG. 1.

EXAMPLE 1

Differential Display

FIG. 1 shows schematically the differential display method applied to genes involved in angiogenesis.

mRNAs are extracted specifically and reverse transcribed using each of the four groups of degenerated anchor oligo (dT) primers, T12MN, in which M can be G, A or C; and N can be G, A, T or C.

Each group of primers is defined by the base of the 3' end (N) with degeneration at the level of the (M) position. For example, the set of primers in which N=G is constituted by:

```
5'-TTTTTTTTTTTTGG-3'  (SEQ ID No.: 1)

5'-TTTTTTTTTTTTAG-3'  (SEQ ID No.: 2)

5'-TTTTTTTTTTTTCG-3'  (SEQ ID No.: 3)
```

The gel diagram schematizes the results of the use of a single primer group with endothelial cells under the three experimental conditions: CR=Reference Condition (endothelial cells in culture with no stimulation), CPA= Angiogenesis Promoting Condition (endothelial cells stimulated by an angiogenic factor selected from among (a), such as FGF2), CIA=Angiogenesis Inhibition Condition (endothelial cells stimulated simultaneously by an angiogenic factor from among (a) and an anti-angiogenic factor from among (b); CC=Control Condition (endothelial cells stimulated by an anti-angiogenic factor selected from among (b)).

The dashed lines of FIG. 1 represent the RNA and the unbroken lines represent the DNA. T12MN is the degenerated oligo(dT) primer; M can be A, G or C (degenerated position); N can be A, C, G or T.

EXAMPLE 2

Subtractive Hybridization

Figure 2:
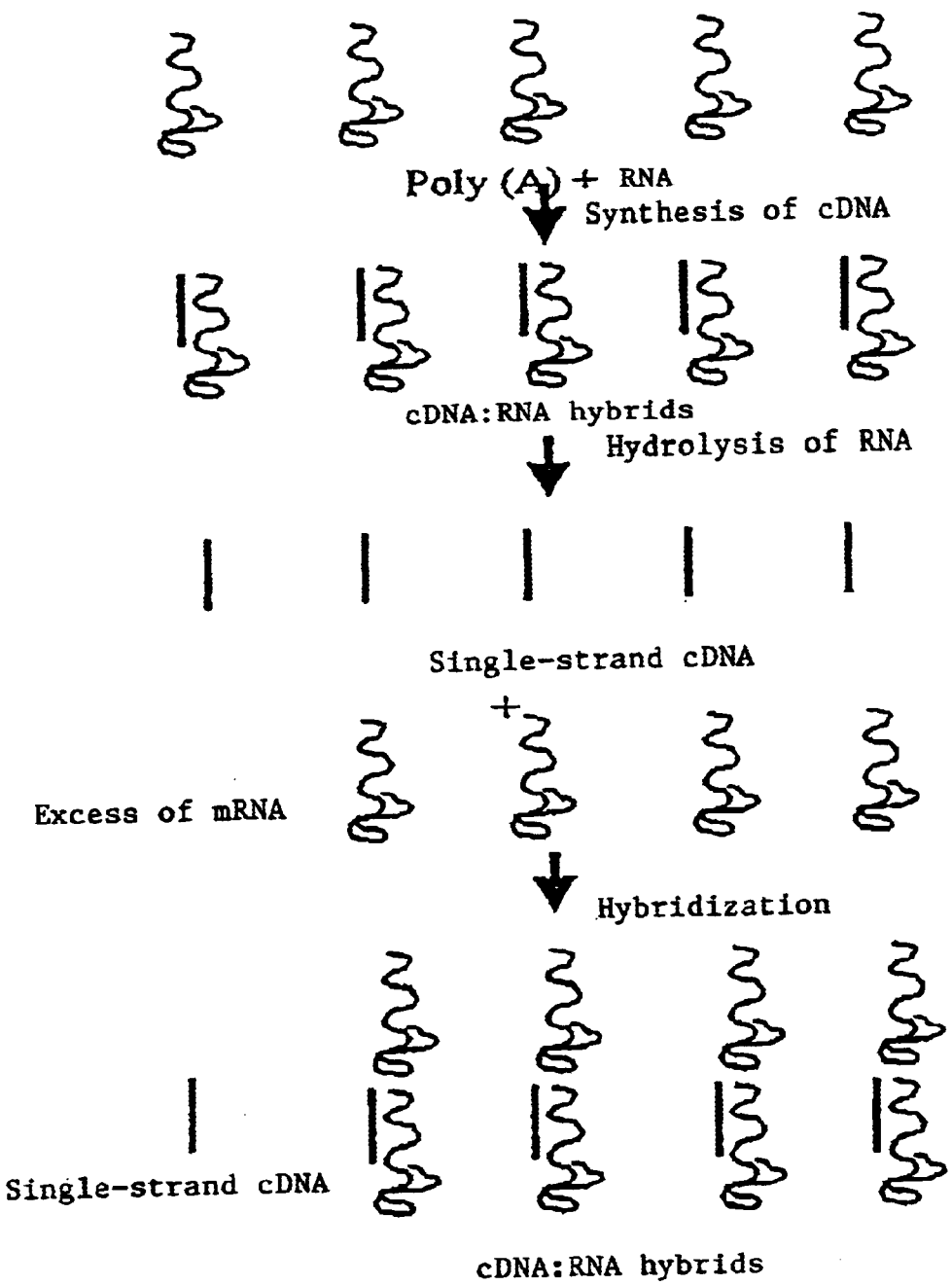
FIGS. 2A and 2B schematically show a method of subtractive hybridization of cDNA in accordance with aspects of the invention.
Figure 2:
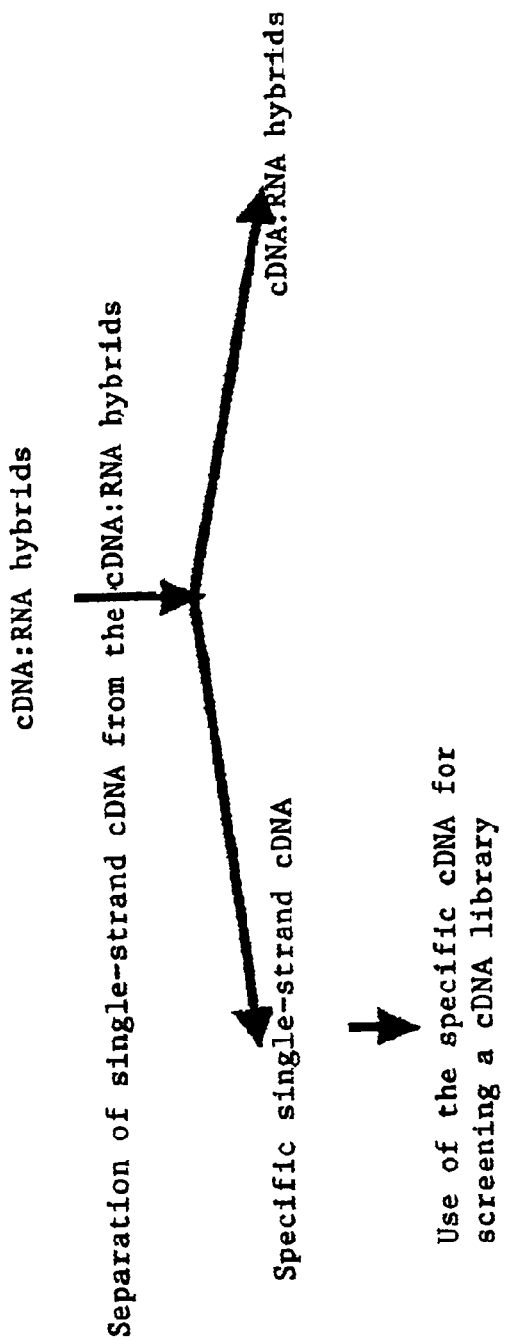

FIG. 2 shows schematically the method for the subtractive hybridization of cDNA.

mRNAs are extracted from cells placed under different operating conditions and reverse transcribed to obtain single-strand cDNAs representing RNA sequences expressed in the cells.

The single-strand cDNA stemming from a cell placed under an operating condition, for example, an angiogenesis stimulating condition is hybridized with an excess of RNA stemming from cells placed under a different operating condition, for example, the reference conditions. In a hybridization reaction of this type, cDNA corresponding to the sequences expressed under both operating conditions will form hybrids with the RNA. In contrast, cDNA which is not represented in the RNA will remain in the form of single-strand cDNA.

Advantageously, by limiting the amount of mRNA used in the hybridization reaction, this method can also be used to isolate a cDNA sequence representing one or more mRNAs overexpressed in cells placed under a given operating condition, for a example, an angiogenesis stimulating condition.

The double-strand cDNA and the single-strand cDNA can be separated, especially by chromatography on a hydroxyapatite column. The single-strand cDNA isolated in this manner corresponds to an mRNA specifically present or overexpressed in the cells placed under a particular culture condition. This cDNA can be used for screening a cDNA library to identify, isolate and clone the corresponding gene.

What is claimed is:

1. A process for identifying genes coding for cellular constituents involved in regulating angiogenesis comprising:
   a) culturing endothelial cells on an extracellular matrix protein according to at least four different types of conditions:
      a reference condition, wherein said cells are not stimulated;
      an angiogenesis promoting condition, wherein said cells are stimulated by an angiogenic factor;
      an angiogenesis inhibiting condition, wherein said cells are stimulated by an angiogenic factor and incubated with one or more anti-antiogenesis factors; and
      a control condition, wherein said cells are incubated with an anti-antiogenesis factor;
   b) isolating messenger RNAs stemming from cells cultured according to the different conditions; and
   c) comparing at the qualitative and/or quantitative level, different messenger RNA populations to identify messenger RNAs stemming from cell cultures under conditions stimulating and/or inhibiting angiogenesis, the messenger RNAs corresponding to the genes coding for the cellular constituents involved in regulating angiogenesis.

2. The process according to claim 1, further comprising:
   d) isolating, amplifying and purifying the messenger RNAs identified in step c);
   e) cloning and sequencing nucleic acid molecules obtained in step d); and
   f) identifying gene(s) corresponding to isolated nucleic acid molecules.

3. The process according to claim 1, wherein the extracellular matrix protein is selected from the group consisting of fibrin, collagen, laminin, Matrigel and fibronectin.

4. The process according to claim 1, wherein the angiogenesis stimulating factors employed in a) is selected from the group consisting of:
   fibroblast growth factors 1 to 15 (FGF 1 to FGF 15),
   epidermis growth factor (EGF),
   vascular endothelial growth factor (VEGF),
   hepatocyte growth factor (HGF),
   platelet derivative growth factor (PDGF), interleukin 8 (IL-8),
angiogenin,
transformant growth factor (TGF),
the neurokine midkine, and
pleiotropin.

5. The process according to claim 1, wherein the anti-angiogenesis factor employed in a) is selected from the group consisting of:
thrombospondin,
angiostatin,
endostatin,
platelet factor 4,
interleukin 10 (IL-10),
interleukin 12 (IL-12),
the chemokines gro-α and β,
the human chondrocyte-derived inhibitor,
leukemia inhibitory factor, and
tumor necrosis factor (TNF).

6. The process according to claim 1, wherein one or more angiogenesis factors added to a cell culture in the form of an expression vector constructed to enable synthesis of the factor(s) in the cell culture.

7. The process according to claim 1, wherein an analysis of the different messenger RNAs is performed by a differential display method comprising:

reverse transcribing the messenger RNAs, separating by electrophoresis DNA molecules obtained by reverse transcription, detecting and then extracting from the electrophoresis support DNA molecules of interest, purifying the DNA molecules of interest, and optionally employing purified DNA molecules as a probe or subcloning and sequencing the purified DNA molecules.

8. The process according to claim 1, wherein analysis of different messenger RNAs is performed by subtractive hybridization.

* * * * *